United States Patent
Mejouev

(10) Patent No.: US 9,581,521 B2
(45) Date of Patent: Feb. 28, 2017

(54) SYSTEMS AND METHODS FOR INSPECTING WOUND OPTICAL FIBER

(71) Applicant: Corning Incorporated, Corning, NY (US)

(72) Inventor: Igor Rafaelyevich Mejouev, Wilmington, NC (US)

(73) Assignee: Corning Incorporated, Corning, NY (US)

( * ) Notice: Subject to any disclaimer, the term of this patent is extended or adjusted under 35 U.S.C. 154(b) by 183 days.

(21) Appl. No.: 14/453,717

(22) Filed: Aug. 7, 2014

(65) Prior Publication Data

US 2015/0070688 A1    Mar. 12, 2015

Related U.S. Application Data

(60) Provisional application No. 61/876,861, filed on Sep. 12, 2013.

(51) Int. Cl.
*G01M 11/00* (2006.01)
*G01N 21/952* (2006.01)
(Continued)

(52) U.S. Cl.
CPC ........... *G01M 11/30* (2013.01); *B65H 63/006* (2013.01); *G01M 11/088* (2013.01);
(Continued)

(58) Field of Classification Search
CPC ............ B65H 2701/30; B65H 2701/32; B65H 63/006; B65H 63/024; B65H 63/028; B65H 63/036; B65H 63/04; B65H 63/06; B65H 63/062; B65H 63/065; B65H 63/08; G01M 11/088; G01M 11/30; G01M 11/37; G01M 11/35; G06T 2207/10016; G06T 2207/20024; G06T 2207/20048; G06T 2207/30108; G06T 2207/0008; G01N 21/88; G01N 21/8803; G01N 21/8806;
(Continued)

(56) References Cited

U.S. PATENT DOCUMENTS 4,672,437 A * 6/1987 Casper .................. G01N 21/88
   348/126
4,928,904 A    5/1990 Watts
(Continued)

FOREIGN PATENT DOCUMENTS

| EP | 0421657 | 4/1991 |
| GB | 2249832 | 5/1992 |
| JP | 1993310370 | 11/1993 |

*Primary Examiner* — Gordon J Stock, Jr.
(74) *Attorney, Agent, or Firm* — Kevin L. Bray

(57) ABSTRACT

Systems and methods for inspecting wound optical fiber to detect and characterize defects are disclosed. The method includes illuminating the wound optical fiber with light from a light source and capturing a digital image based on measurement light that is redirected by the wound optical fiber to a digital camera. The method also includes processing the digital image with a computer to detect and characterize the defects. The types of defects that can be detected using the systems and methods disclosed herein include bubbles, abrasions, punctures, scratches, surface contamination, winding errors, periodic dimensional errors, aperiodic dimensional errors and dents.

20 Claims, 19 Drawing Sheets

(51) Int. Cl.
*G01N 21/896* (2006.01)
*G01N 21/958* (2006.01)
*B65H 63/00* (2006.01)
*G06T 7/00* (2006.01)
*G01N 21/88* (2006.01)
*G01N 21/95* (2006.01)
*G01M 11/08* (2006.01)

(52) U.S. Cl.
CPC ............ *G01M 11/35* (2013.01); *G01M 11/37* (2013.01); *G01N 21/896* (2013.01); *G01N 21/952* (2013.01); *G01N 21/958* (2013.01); *G06T 7/0008* (2013.01); *B65H 2701/32* (2013.01); *G01N 2021/8887* (2013.01); *G01N 2021/8965* (2013.01); *G01N 2021/9511* (2013.01); *G06T 2207/10016* (2013.01); *G06T 2207/20024* (2013.01); *G06T 2207/20048* (2013.01); *G06T 2207/30108* (2013.01)

(58) Field of Classification Search
CPC .... G01N 21/896; G01N 21/95; G01N 21/952; G01N 21/958; G01N 2021/8444; G01N 2021/8808; G01N 2021/8835; G01N 2021/8841; G01N 2021/8854; G01N 2021/8858; G01N 2021/8861; G01N 2021/8864; G01N 2021/8867; G01N 2021/887; G01N 2021/8874; G01N 2021/8877; G01N 2021/888; G01N 2021/8887; G01N 2021/889; G01N 2021/8893; G01N 2021/8896; G01N 2021/8962; G01N 2021/8965; G01N 2021/8967; G01N 2021/9511

See application file for complete search history.

(56) References Cited

U.S. PATENT DOCUMENTS

| | | | |
|---|---|---|---|
| 5,786,891 A | 7/1998 | Jakobsen et al. | |
| 6,633,383 B1* | 10/2003 | Jackson | B65H 63/006 356/238.2 |
| 2012/0050523 A1* | 3/2012 | Cook | H04N 7/188 348/92 |

* cited by examiner

SYSTEMS AND METHODS FOR INSPECTING WOUND OPTICAL FIBER

This application claims the benefit of priority under 35 U.S.C. §119 of U.S. Provisional Application Ser. No. 61/876,861 filed on Sep. 12, 2013 the content of which is relied upon and incorporated herein by reference in its entirety.

FIELD

The present disclosure relates to optical fiber inspection and in particular relates to inspecting wound optical fiber.

BACKGROUND

The fabrication of optical fibers generally involves subjecting a preform to heat and drawing the preform under tension to create the optical fiber. A number of other operations, such as coating, are usually performed as part of the fabrication process. The final optical fiber is typically wound onto a storage spool that can accommodate from many hundreds of meters up to many kilometers of optical fiber.

The optical fiber is inspected during the fabrication process. Such inspections are typically performed on the optical fiber as an isolated strand prior to the optical fiber being wound upon itself on the spool for storage.

Presently, the inspection of optical fibers on storage spools is done manually and is thus a tedious and labor-intensive operation. During the manual inspection, an operator has to visually check the wound fiber for many different types of defects, with some defects being easier to spot than others. For example, abrasions and micro-defects in the optical fiber coating (e.g., bubbles and punctures) are easily missed in view of the optical fiber's bright reflective surface and small diameter. Moreover, one layer of optical fiber on the storage spool can represent over a thousand windings, which makes the inspection process daunting.

SUMMARY

A first aspect of the disclosure is a method of inspecting a wound optical fiber on a spool. The method includes illuminating the wound optical fiber with illumination light from at least a first illumination direction; capturing from at least one detection direction at least one digital image of illumination light that is redirected from the wound optical fiber as measurement light; and processing the at least one digital image to detect and characterize at least one defect of the wound optical fiber.

Another aspect of the disclosure is a method of inspecting a wound optical fiber. The method includes: illuminating the wound optical fiber to generate measurement light; rotating the wound optical fiber; capturing a plurality of digital images of the wound optical fiber based on the measurement light during the rotation; and processing the plurality of digital images to characterize at least one defect of the wound optical fiber.

Another aspect of the disclosure is a system for inspecting a wound optical fiber on a spool. The system includes: a first light source arranged to illuminate the wound optical fiber with light from a first illumination direction; a digital camera arranged to capture from a detection direction at least one digital image of light that is at least one of reflected and scattered from the wound optical fiber; and a computer adapted to process the at least one digital image to characterize at least one defect of the wound optical fiber.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary and are intended to provide an overview or framework for understanding the nature and character of the claims.

BRIEF DESCRIPTION OF THE DRAWINGS

The accompanying drawings are included to provide a further understanding and are incorporated in and constitute a part of this specification. The drawings illustrate one or more embodiment(s), and together with the Detailed Description serve to explain principles and operation of the various embodiments. As such, the disclosure will become more fully understood from the following Detailed Description, taken in conjunction with the accompanying Figures, in which:

FIGS. 5A and 6A are digital images of two different spools of wound optical fiber taken using the measurement system of FIG. 3A, while

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute a part of this Detailed Description.

The entire disclosure of any publication or patent document mentioned herein is incorporated by reference.

Cartesian coordinates are shown in some of the Figures for the sake of reference and are not intended to be limiting as to direction or orientation.

Figure 1A:
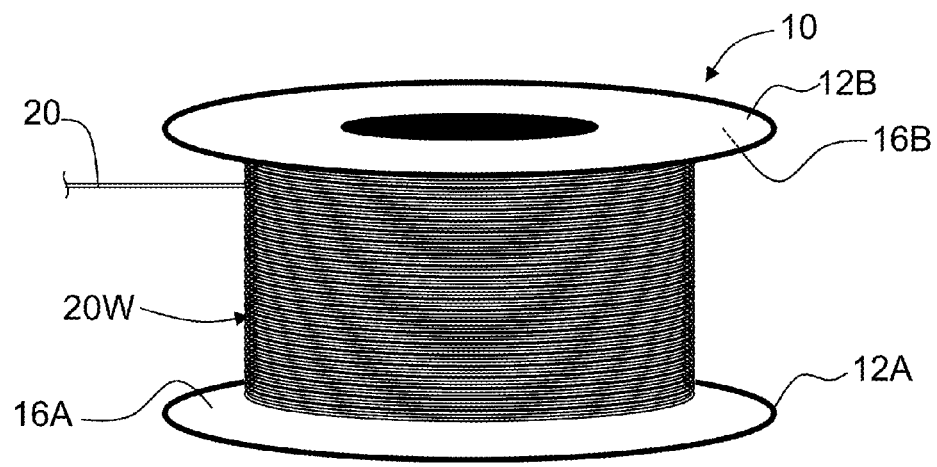
FIG. 1A is an elevated view of an example spool that contains wound optical fiber.
Figure 1B:
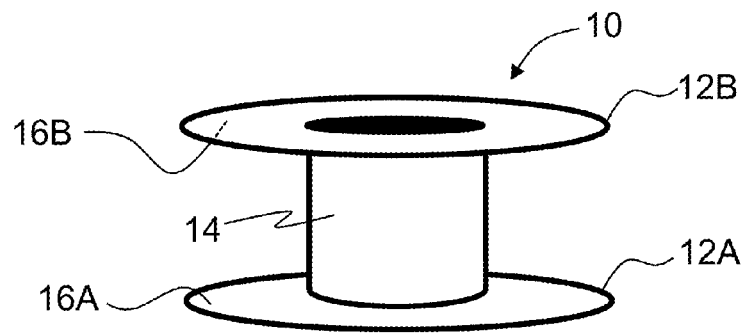
FIG. 1B is an elevated view of an empty spool.

FIG. 1A is an elevated view of an example spool 10 that includes an optical fiber 20 wound around and thus stored on the spool. FIG. 1B is an elevated view of an empty spool 10. The spool 10 includes flanges 12A and 12B connected by a central cylindrical post 14 around which optical fiber 20 can be wound. The flanges 12A and 12B include respective inner surfaces 16A and 16B. The length of optical fiber 20 stored on spool 10 can range from tens or hundreds of meters to many kilometers. There may be thousands of windings of optical fiber 20 on spool 10. The optical fiber 20 as wound on spool 10 is referred to herein as "wound optical fiber" 20W. The optical fiber 20 can be any type of optical fiber that would benefit from being inspected after it is wound onto spool 10. Reference to spool 10 below refers to a spool that includes wound optical fiber 20W unless otherwise stated.

Figure 2:
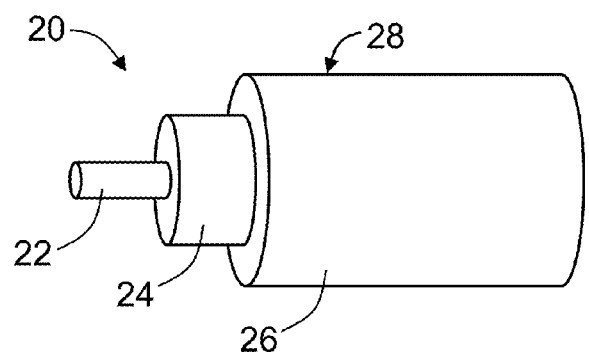
FIG. 2 is a partial cutaway view of an example optical fiber.

FIG. 2 is a partial cutaway view of an example optical fiber 20 and shows a core 22, a cladding 24 that surrounds the core, and a buffer coating ("coating") 26 that surrounds the cladding. The coating 26 has an outer surface 28 that defines the outer surface of optical fiber 20. The wound optical fiber 20W can have one or more defects, such as bubbles, abrasions, punctures, scratches, surface contamination, cracks, breaks, winding errors, periodic dimensional errors, aperiodic dimensional errors and dents.

First Embodiment

Figure 3A:
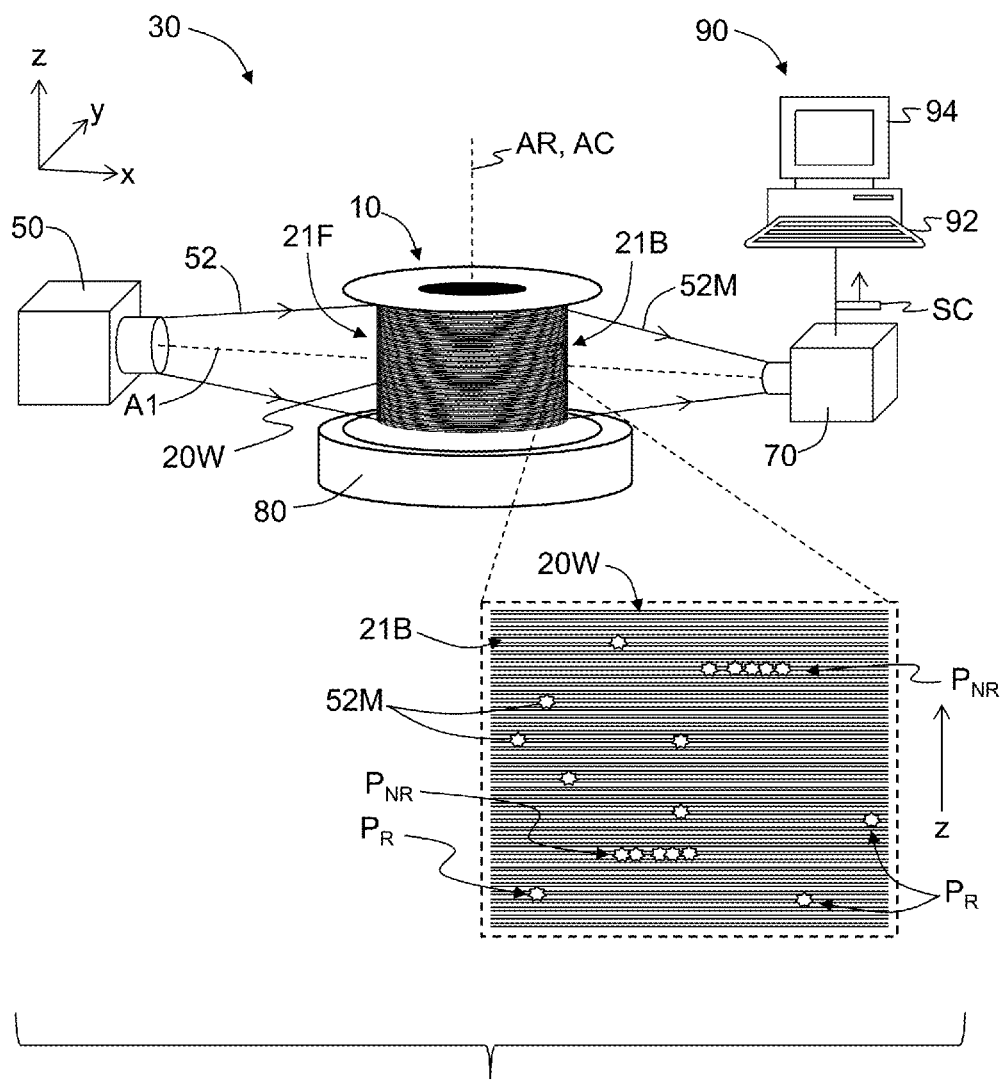
FIG. 3A is an elevated view of an example measurement system configured to perform a measurement of the wound optical fiber to detect defects therein according to a first embodiment.

FIG. 3A is an elevated view of a measurement system 30 configured for performing a measurement of defects in wound optical fiber 20W according to a first embodiment. The measurement system 30 includes a light source 50 that emits illumination light 52, and a digital camera 70. The light source 50 and digital camera 70 are arranged along an axis A1, and spool 10 is arranged along axis A1 between the light source and the digital camera so that the light source and the digital camera face substantially opposite sides of wound optical fiber 20W. In an example, the illumination direction and the detection direction are oriented substantially 180° apart relative to spool 10. A front side 21F of wound optical fiber 20W faces light source 50, while a back side 21B faces digital camera 70. The light 52 that reaches digital camera 70 via wound optical fiber 20W is referred to herein as measurement light 52M.

Figure 3B:
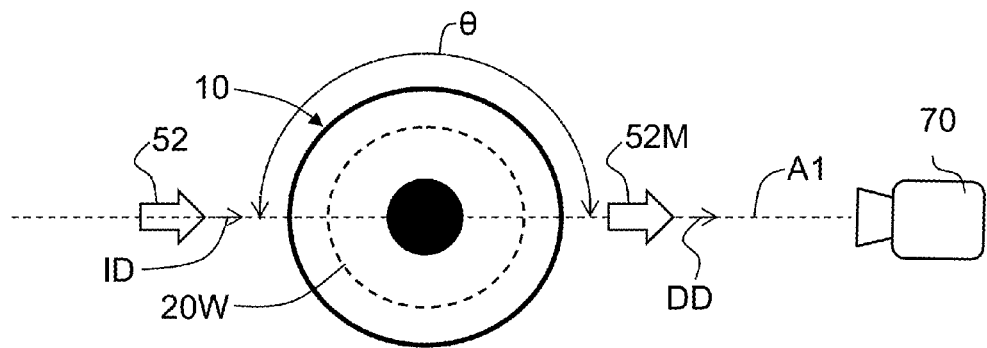
FIG. 3B is a schematic top-down view of the measurement system of FIG. 3A, showing the illumination and detection directions and the measurement angle.

FIG. 3B is a top-down schematic view of a portion of system 30 that shows the illumination direction ID for illumination light 52 incident upon wound optical fiber 20W and the direction of measurement light 52M (i.e., detection direction DD) as received by digital camera 70.

The digital camera 70 is configured to capture one or more digital images (e.g., a still image, a sequence of digital images, video images, etc.) and generate camera signals SC that electronically embody the one or more digital images. The spool 10 is supported by a support member 80, such as a stage. Support member 80 may include an axle (see FIG. 13A, introduced and discussed below). In an example, support member 80 is rotatable about a rotation axis AR that corresponds to a central axis AC of the cylindrical spool 10. In another example, support member is fixed and allows for spool 10 to rotate (e.g., about the aforementioned axle). In an example, spool 10 is driven (e.g., by a rotating rubber wheel (not shown) pressed against one of flanges 12A or 12b) so that it rotates about its central axis AC.

The measurement system 30 has a computer 90 electrically connected to digital camera 70. The computer 90 can be any type of computer, such as a personal computer or workstation. The computer 90 preferably includes any of a number of commercially available micro-processors, a suitable bus architecture to connect the processor to a memory device, such as a hard disk drive, and suitable input and output devices (e.g., a keyboard 92 and a display 94). The computer 90 can be programmed via instructions (software) embodied in a computer-readable medium (e.g., memory, processor, etc.) that cause the computer to process camera signals SC to characterize one or more defects in wound optical fiber 20W.

In an example, computer 90 includes instructions embodied in a computer-readable medium for performing at least one of the following processes: an edge detection, an average, a correlation, an autocorrelation, a convolution, a de-convolution, a Fourier transform and a filter (i.e., a filter process or filtering).

In the operation of measurement system 30, light source 50 emits light 52 that illuminates front side 21F of wound optical fiber 20W. A portion of light 52 couples into coating 26 of wound optical fiber 20W and travels to back side 21B of the wound optical fiber, whereupon the trapped light exits outer surface 28 of the coating (e.g., by scattering) as measurement light 52M, which is detected by digital camera 70.

The close-up inset of FIG. 3A shows a portion of wound optical fiber 20W at back side 21B. The coating 26 has defects such as bubbles, punctures, etc. that give rise to scattered measurement light 52M that appears as bright dots in an example digital image 72 captured by digital camera 70.

Figure 4A:
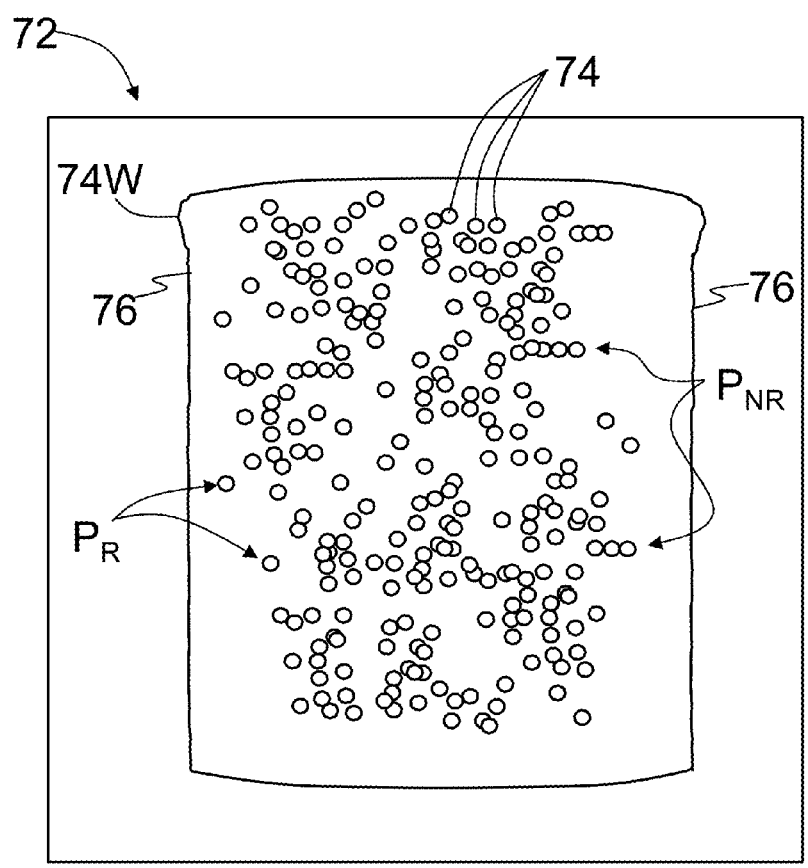
FIG. 4A is an example representation of a processed digital image captured by a digital camera of the measurement system, wherein the positions of the defects are calculated based on scattered measurement light.

FIG. 4A is an example representation of the processed digital image 72 captured by digital camera 70. The processed digital image 72 shows defects 74 calculated based on the detected scattered measurement light 52M. The processed digital image 72 also shows the calculated edges 76 of wound optical fiber 20W. A winding defect 74W is shown near flange 12A (not shown in FIG. 4A). The winding defect 74W shows how optical fiber 20 was not wound evenly and so is bunched up at flange 12A. This is indicative of a winding problem when optical fiber 20 was wound onto spool 10, and the winding problem may have caused other defects in wound optical fiber 20W.

In an example embodiment, digital camera 70 can zoom in on back side 21B of wound optical fiber 20W to get a closer look at scatted light 52M. In another embodiment, a different camera (not shown) with microlenses can be used to obtain a more close-up view of back side 21B. In an example, a deconvolution process (e.g., a deconvolution algorithm run on computer 90) is used to process digital image 72 (or multiple digital images) to obtain the defect positions. Position analysis can be used to filter out scattered light 52M that originates from random positions $P_R$ that can represent dust particles or punctures while detecting scattered light from non-random positions $P_{NR}$, such as aligned positions that can represent coating bubble defects (see also FIG. 3A). The density and linear distribution of defects 74 are then calculated, and the defect count is compared to a defect count threshold, e.g., for a pass/fail judgment.

Figure 4B:
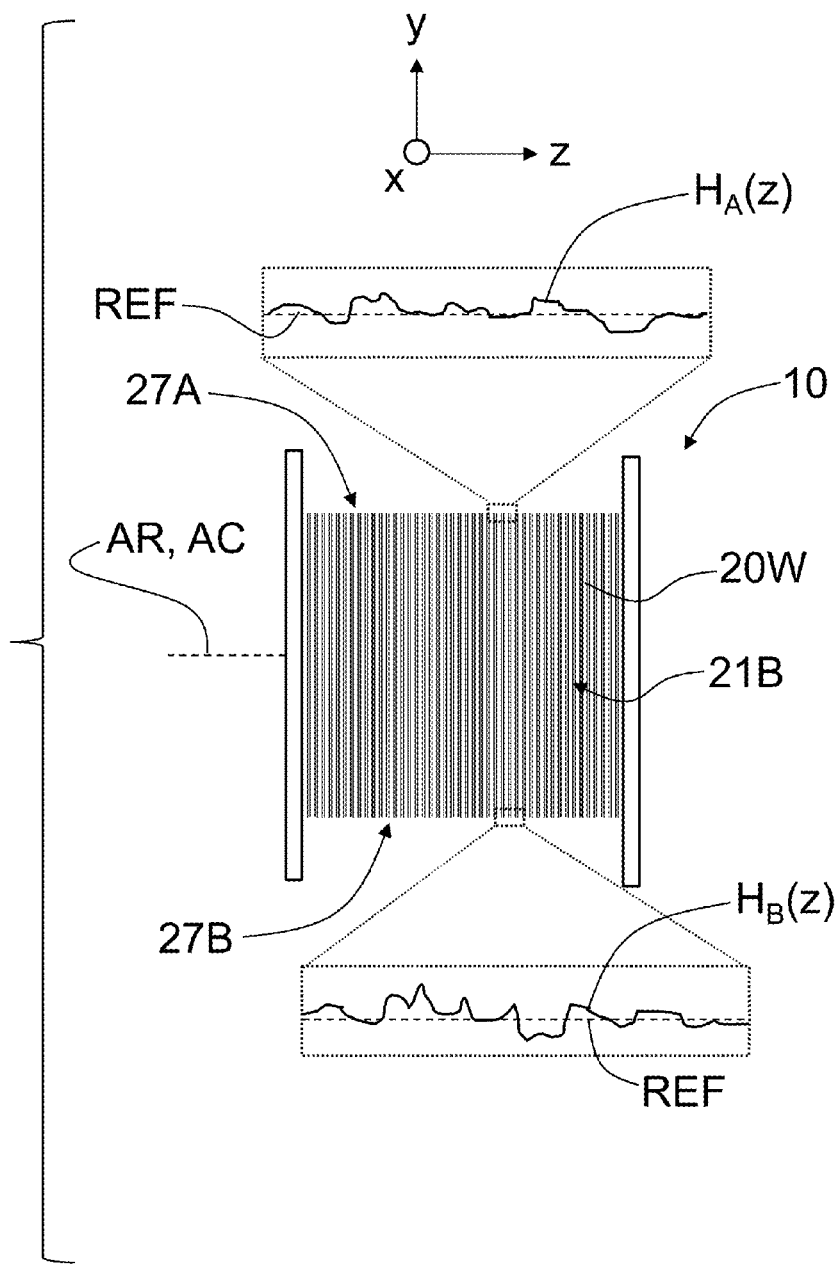
FIG. 4B is a back-side view of the spool, showing in the close-up insets how the digital image contains information about the intensity variation at the edges of the wound optical fiber as seen by the digital camera along a detection direction.

FIG. 4B shows spool 10 as viewed in the direction of back side 21B, i.e., as seen by digital camera 70. From this view, wound optical fiber 20W has edges 27A and 27B. In an example, edges 27A and 27B are measured and compared to a reference REF, e.g., a straight edge or line. The variation in edge heights $H_A(z)$ and $H_B(z)$ is measured and compared to threshold values.

In various examples, the two measured edge heights $H_A(z)$ and $H_B(z)$ are compared. Example comparisons include calculating $\Delta H(z)=H_A(z)-H_B(z)$, a best fit polynomial calculation, $|\Delta H|=|H_A(z)-H_B(z)|$, $H_A*H_B$ (convolution) or $H_A \star H_B$ (correlation), a deconvolution $F\{H_A(z)\}\cdot F\{H_A(z)\}$ (where F denotes the Fourier transform), or similar comparison-type functions used in the art to perform statistical analysis of two sets of measurement data.

FIG. 4B includes insets that show close-up views of respective portions of measured edges 27A and 27B showing $H_A(z)$ and $H_B(z)$ along with reference REF. In an example, the measured heights $H_A(z)$ and $H_B(z)$ are filtered to remove high-frequency components associated with individual optical fibers 20 so that the lower-frequency variations as a function of the z-position (i.e., along the edges 27A and 27B) are more easily discerned. In an example, standard edge detection algorithms can be used to detect bright edges 27A and 27B against a dark background.

Figure 5A:
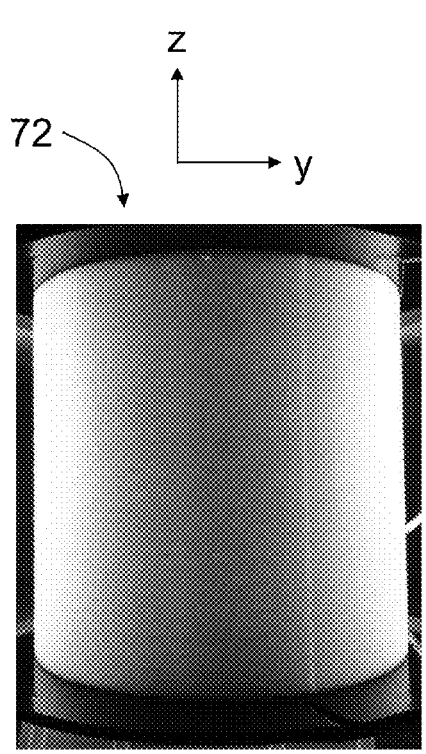
Figure 6A:
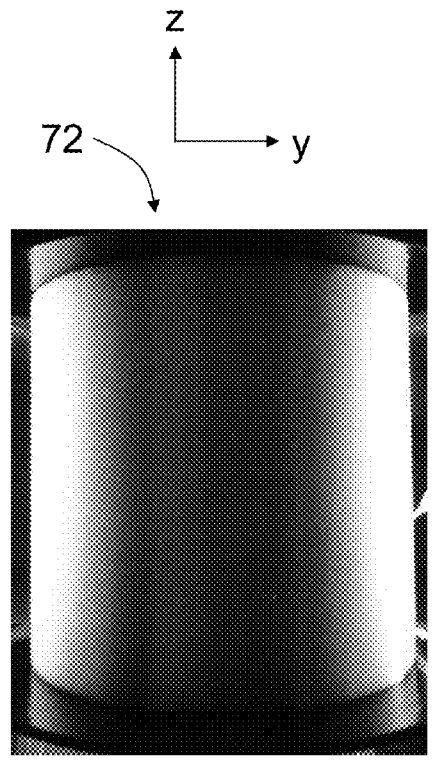

FIGS. 5A and 6A are two images 72 of two different spools of wound optical fiber 20W as taken by digital camera 70 and illuminated by light source 50 using the configuration of system 30 of FIG. 3A. The image 72 of FIG. 5A has a higher light intensity in the central region and a smaller dynamic range of contrast (pale fiber) than the image of FIG. 6A, which indicates higher scattering caused by micro-abrasions along the entire length of wound optical fiber 20W.

Figure 5B:
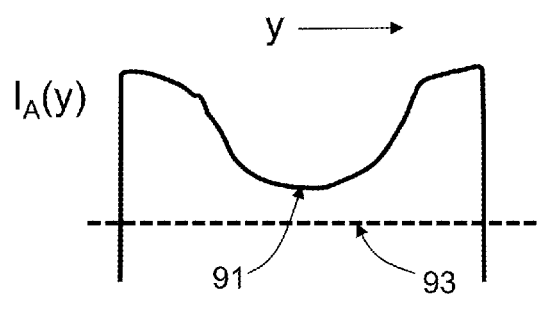
FIGS. 5B and 6B are plots of the average intensity $I_A(y)$ versus y-position for the digital images of FIGS. 5A and 6A, respectively, wherein the plots show valleys having a depth that is above a threshold (FIG. 5B) and that is below the threshold (FIG. 6B)
Figure 6B:
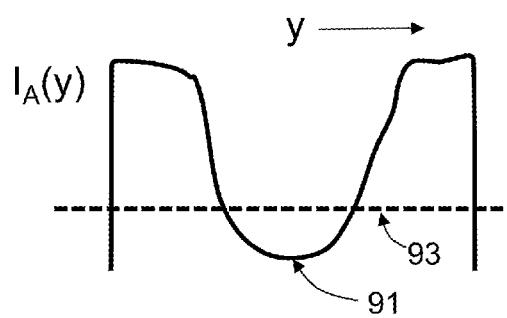

FIGS. 5B and 6B plot the average light intensity distribution $I_A(y)$ for the images 72 of FIGS. 6A and 6B, respectively. The average intensity $I_A(y)$ for each y position can be calculated as $I_A(y)=\Sigma I_A(z,y)/N$ or by taking a median value of some subset of N pixels along the z direction. The middle depth, slopes, total area of the curve, integrated residual $\Sigma(I_A(y)-I_E(y))$ (for $I_E$="expected intensity", i.e., an ideal or "good" intensity) or some other metric values derived from intensity curves $I_A(y)$ can be used to compare to thresholds for a pass/fail judgment for spool 10. Threshold values can be derived from analyzing metrics values of good spools 10. Thresholds can also be a function of the coating type, the fiber length of each spool 10, and like properties.

In the plots of FIGS. 5B and 6B, the depth of valley 91 is compared to a threshold value 93. In the plot of FIG. 5B, valley 91 lies above threshold 93, indicating that wound optical fiber 20W has an unacceptable level of micro-abrasion defect. The plot of FIG. 6B shows that spool 10 has an acceptable depth for valley 91, i.e., the valley extends below threshold 93, indicating an acceptable level of micro-abrasion.

In an example, the measurement process can be repeated using multiple digital images 72 taken with different exposures to cover a large dynamic range in the digital images and with different rotational positions of spool 10 to cover the entire circumference of wound optical fiber 20W.

Second Embodiment

Figure 7A:
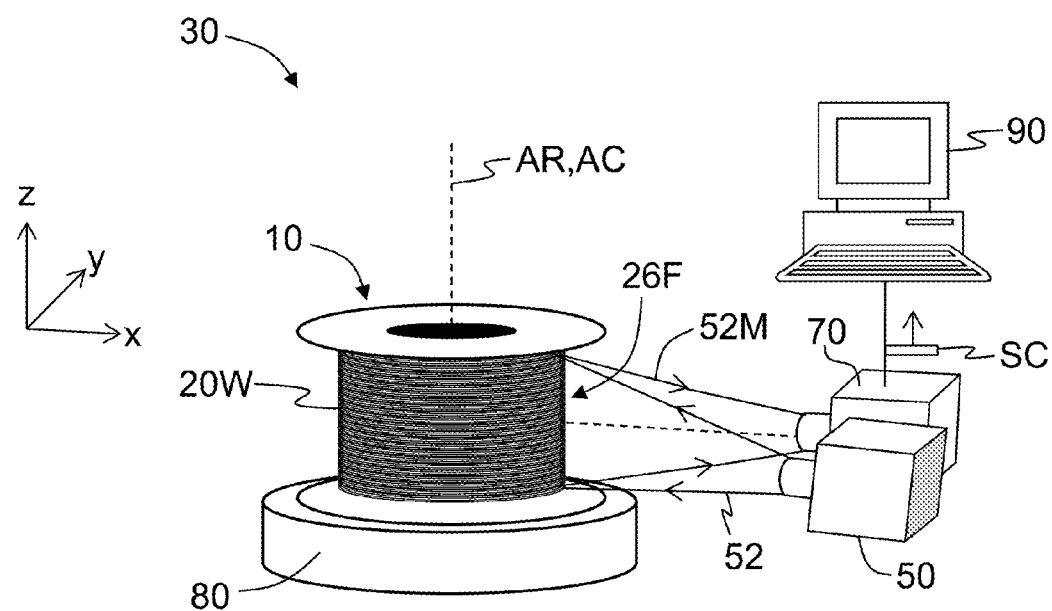
FIG. 7A is similar to FIG. 3A and shows an example configuration of the measurement system as configured to perform a measurement of the wound optical fiber to detect defects therein according to a second embodiment.
Figure 7B:
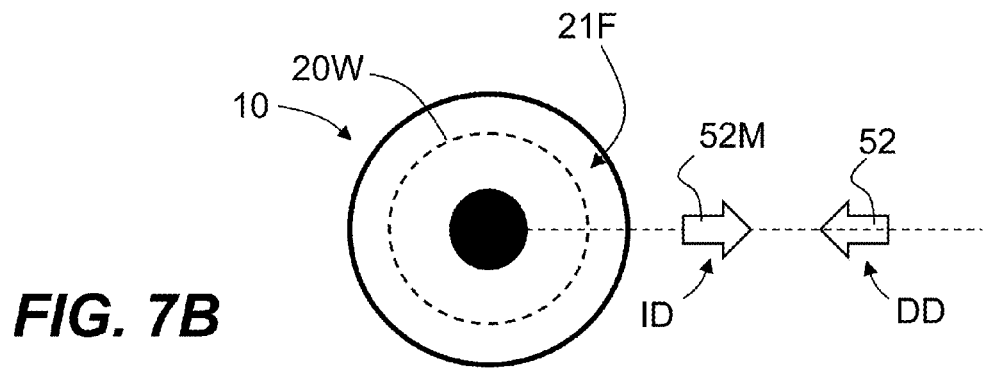
FIGS. 7B through 7D are schematic top-down views of the measurement system of FIG. 7A, showing the illumination and detection directions for three variations of the example configuration of the measurement system of FIG. 7A.
Figure 7C:
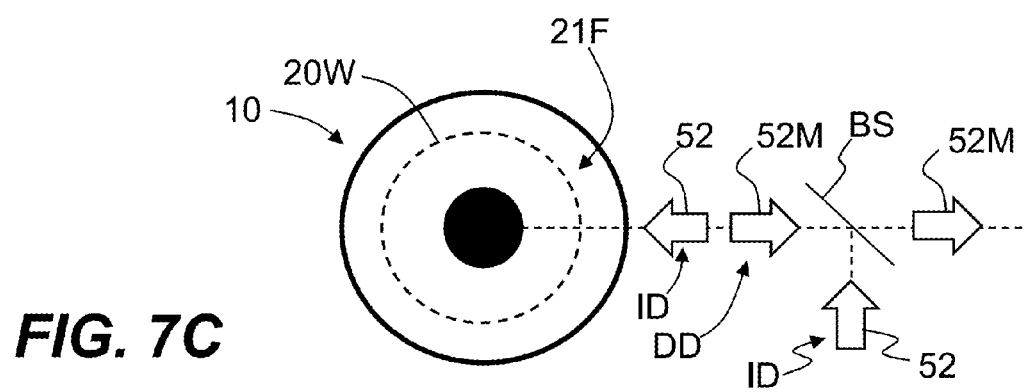
Figure 7D:
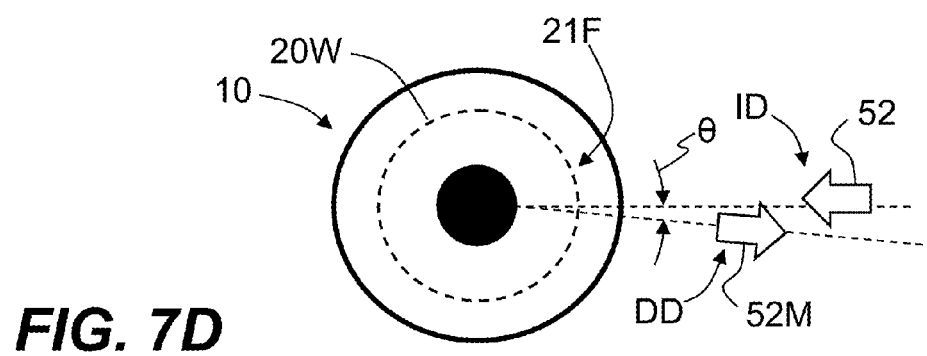

FIG. 7A shows an example configuration of measurement system 30 similar to that of FIG. 3A, but wherein light source 50 and digital camera 70 are on a front side 26F of wound optical fiber 20W, and in an example, have a small angular separation or no angular separation. FIGS. 7B through 7D are schematic top-down views similar to FIG. 3B, showing the incident illumination direction ID of illumination light 52 and the detection direction DD of measurement light 52M as detected by digital camera 70. FIG. 7C shows an example where a beamsplitter BS is used to allow for illumination light 52 and measurement light 52M to share a portion of the same optical path, i.e., the same direction. FIG. 7C shows an embodiment wherein there is a small measurement angle θ between the illumination and detection directions, e.g., θ≤10°.

Figure 8A:
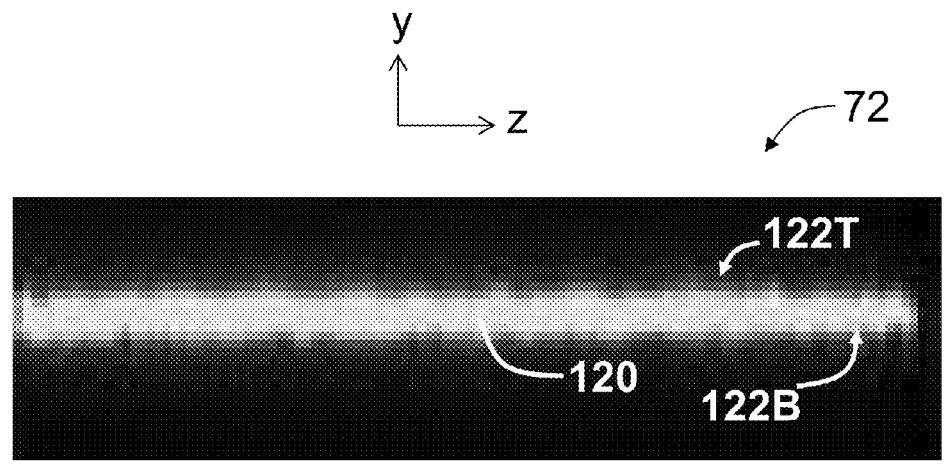
FIGS. 8A and 8B are two example digital images of the front side of a wound optical fiber as obtained using the measurement system of FIG. 7A, wherein the illumination creates a saturated reflection line that can be processed to extract defect information.
Figure 8B:
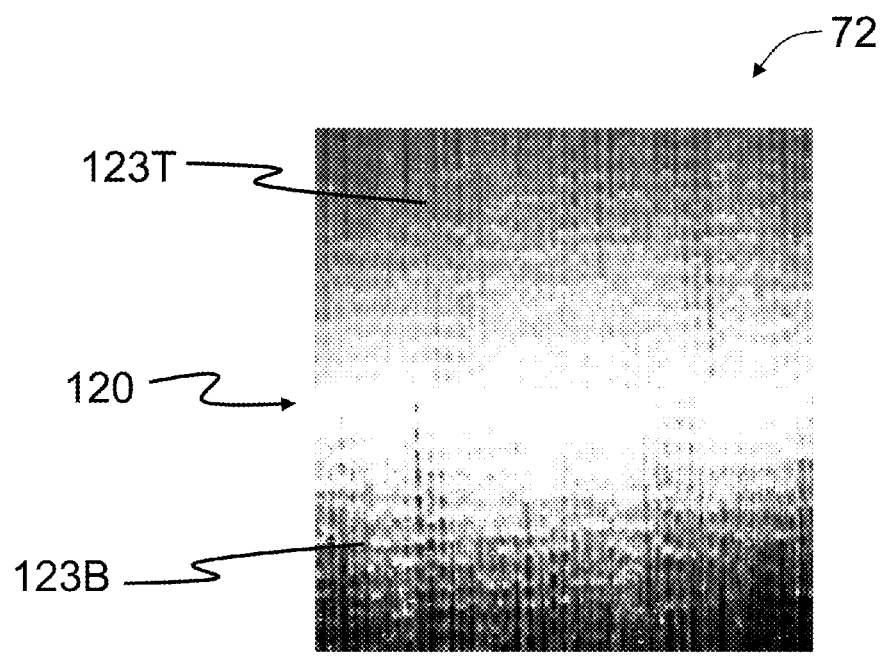
Figure 8C:
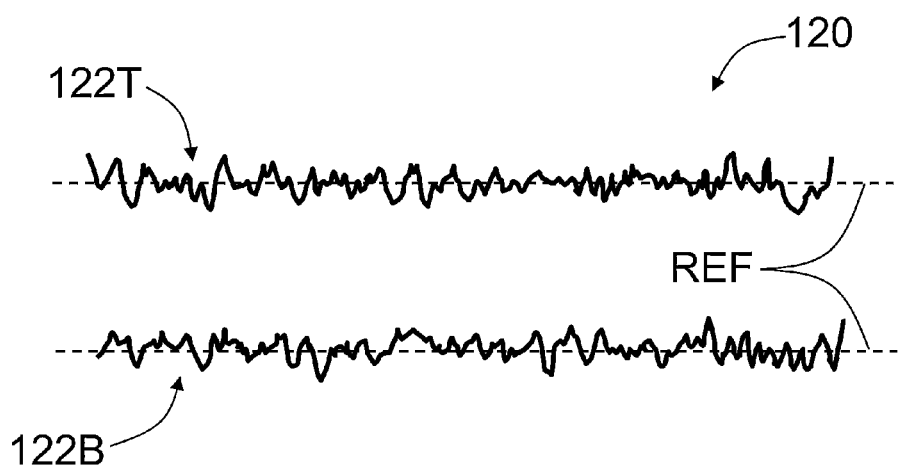
FIG. 8C is a schematic representation of edge measurements for the top and bottom edges of the reflection line of FIG. 8A, along with reference lines.

In this second embodiment, measurement light 52M returns to digital camera 70 substantially along the direction of illumination light 52. The cylindrical front surface 21F defined by wound optical fiber 20W creates a saturated reflection line 120, as shown in digital images 72 of FIGS. 8A and 8B. The reflection line 120 has top and bottom edges 122T and 122B, respectively, which can be processed by computer 90 to extract defect information. FIG. 8C is a schematic representation of edge measurements for top and bottom edges 122T and 122B extracted from reflection line 120 of digital image 72 of FIG. 8A. Reference lines REF are also shown.

If optical fiber 20 has a defect in the form of a periodic or quasi-periodic variation in the coating diameter, then the cylindrical surface of wound optical fiber 20W will have micro-variations that will periodically or quasi-periodically alter the angle of reflection from that expected from the wound optical fiber if made from perfect optical fiber. The periodic or quasi-periodic coating diameter imperfection manifests itself as periodic or quasi-periodic variations in light intensity 123T and 123B along axis Y on both sides of the saturated edges.

Figure 8D:
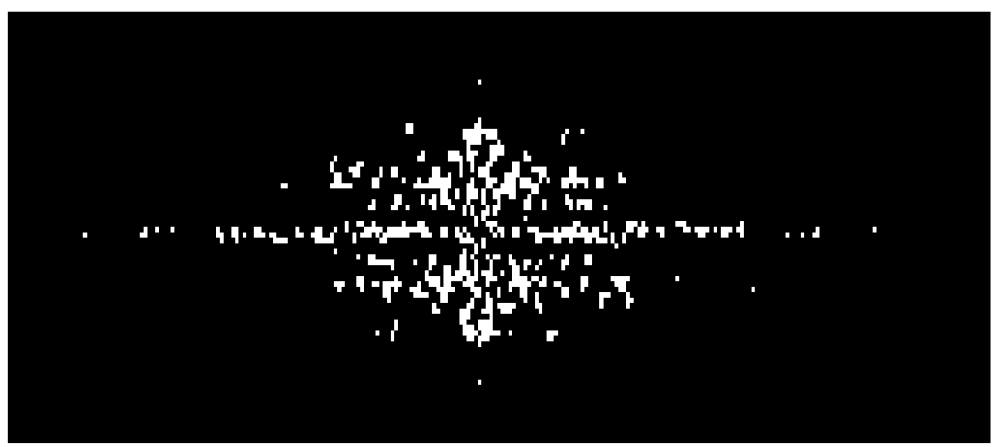
FIG. 8D is a 2D Fourier transform of top and bottom regions of the digital image of FIG. 8B, and shows characteristics of a periodic defect in the fiber-coating diameter.

In an example, computer 90 performs a 2D Fourier analysis of at least a portion of digital image 72. FIG. 8D is a 2D Fourier transform of top and bottom regions 123T and 123B of digital image 72 of FIG. 8B and has the signature of a periodic or quasi-periodic defect 74 in the thickness of coating 26. Such a defect 74 falls into the category of a periodic dimensional error.

Third Embodiment

Figure 9A:
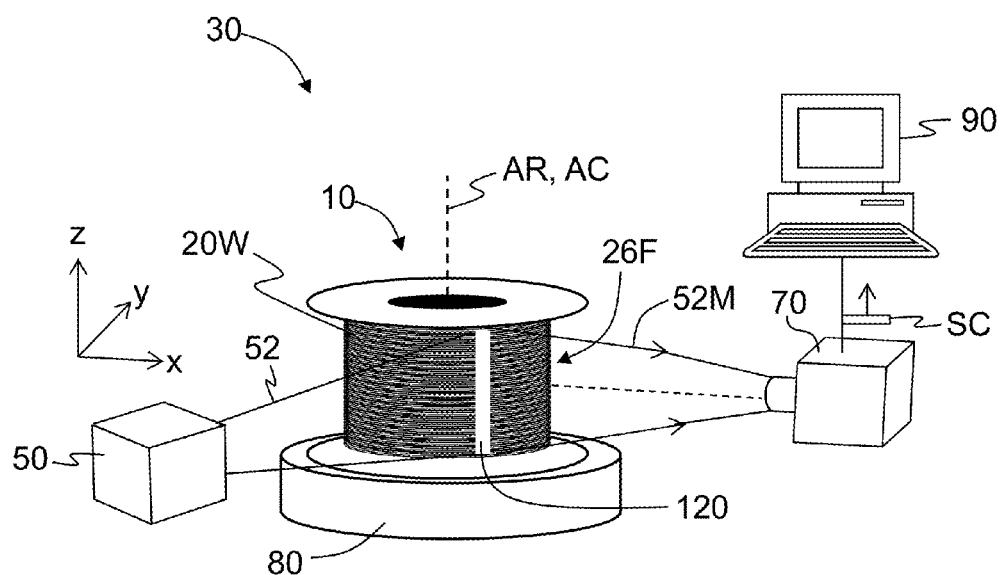
FIG. 9A is similar to FIGS. 3A and 7A and shows an example measurement system as configured to perform a measurement of the wound optical fiber to detect defects therein according to a third embodiment.

FIG. 9A shows an example configuration of measurement system 30 similar to that of FIGS. 3A and 7A, but wherein light source 50 and digital camera 70 are arranged so that the illumination direction of illumination light 52 and the detection direction of measurement light 52M define a measurement angle θ in the range from about 80° to about 150°, e.g., about 130°.

Figure 9B:
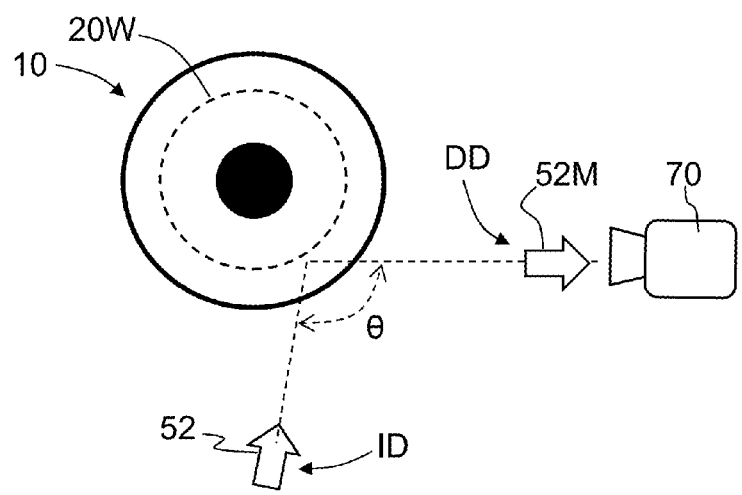
FIG. 9B is a schematic top-down view of the measurement system of FIG. 9A showing the showing the illumination and detection directions and the measurement angle.

FIG. 9B is a schematic top-down view of the measurement system 30 of FIG. 9A showing the illumination light 52 traveling along an illumination direction ID to wound optical fiber 20W, and the measurement light 52M traveling along a detection direction DD from the wound optical fiber to digital camera 70. The measurement angle θ between the illumination direction ID and detection direction DD is also shown.

Figure 10:
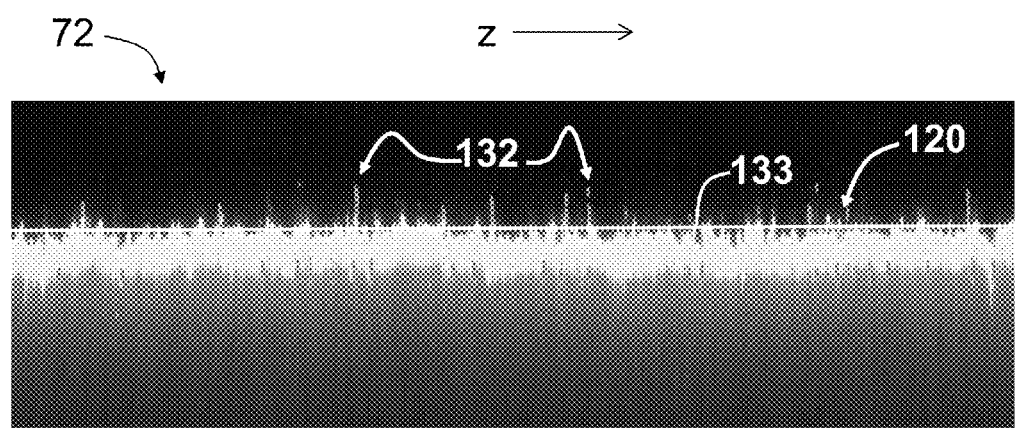
FIG. 10 is a digital image of wound optical fiber illuminated using the measurement system of FIG. 9A.

FIG. 10 is a digital image 72 of wound optical fiber 20W illuminated using measurement system 30 configured as shown in FIGS. 9A and 9B. Similar to the second embodiment, a bright saturated region (line) 120 of directly reflected measurement light 52M from the surface of the top layer of wound optical fiber 20W is analyzed. An edge detection algorithm used to find shape of a top edge 133 of the reflection. A median filter is used to smooth top edge 133. Single stand-alone spikes 132 above the smoothed top edge 133 that indicate single fiber threads with high-frequency variations in coating diameter and short regions of abrasions are counted. The defect count is compared to a threshold count for a pass/fail determination for spool 10.

Fourth Embodiment

Figure 11A:
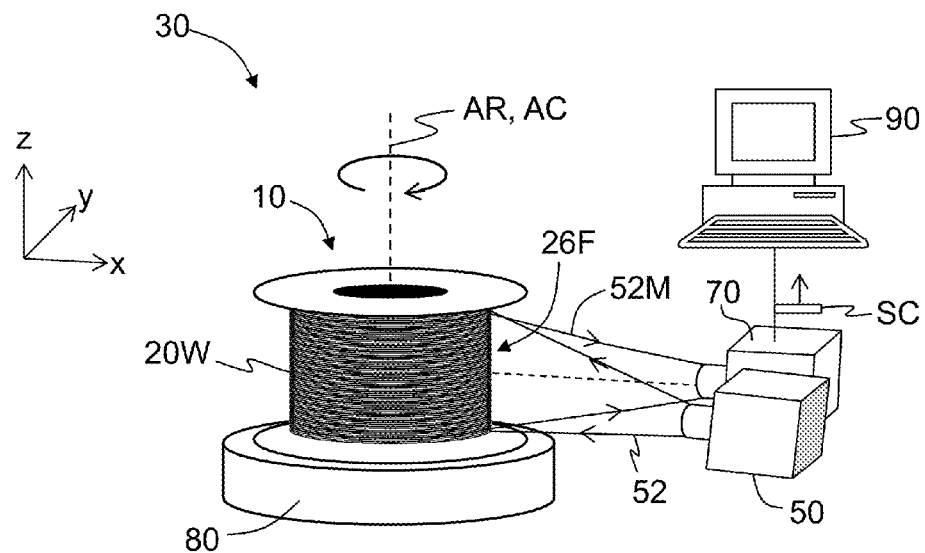
FIG. 11A is similar to FIGS. 3A, 7A and 9A and shows an example configuration of the measurement system for performing a measurement of defects in the wound optical fiber according to a fourth embodiment.
Figure 11B:
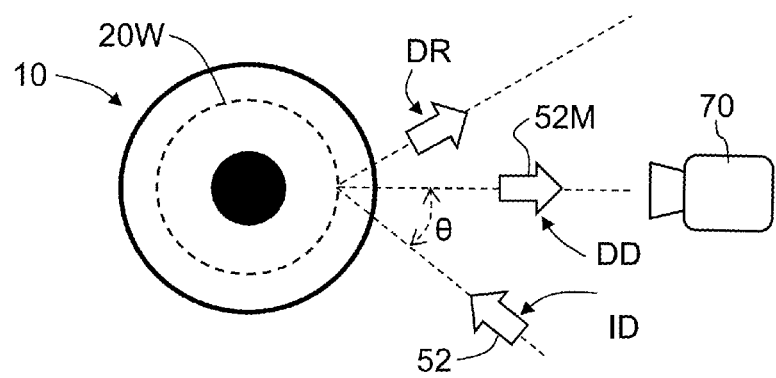
FIG. 11B is a schematic top-down view of the measurement system of FIG. 11A, showing the illumination and detection directions and the measurement angle.

FIG. 11A shows an example configuration of measurement system 30 similar to that of FIG. 7A, wherein digital camera 70 is positioned to receive diffused measurement light 52M rather than directly reflected measurement light. FIG. 11B is a schematic top-down view of the measurement system 20 of FIG. 11A, showing the illumination direction ID, a direct reflection direction DR and the detection direction DD, along with the measurement angle θ.

To perform a measurement with measurement system 30 of FIG. 11A, spool 10 is rotated 360° while digital camera 70 captures a sequence of N digital images (e.g., video images), e.g., tens to hundreds of frames. Pixels inside of a narrow region 135 (mY pixels high, e.g. one to tens of pixel high) of each digital image 72 far above or below direct reflection line 120 (see FIG. 12A) is then processed and analyzed to detect any non-uniformity of diffuse reflected measurement light 52M in narrow region 135. Such non-uniformities are typically caused by abrasion, surface contamination and dust particles. Example processing includes calculating maximum, average or median values of all mY pixels of narrow region 135 in each Z position. The result of each image processing is an intensity function $<I_n(z)>$ for the particular image n.

Figure 12A:
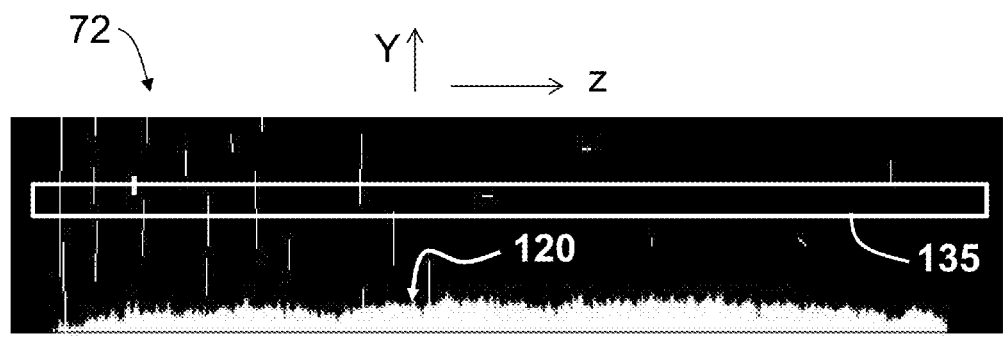
FIG. 12A is a portion of a digital image captured using the measurement system of FIG. 11A, and shows the measurement light having a direct reflection (bottom) from the light source and narrow region inside of which diffused reflection measurement light is analyzed.

FIG. 12A is a portion of an example digital image 72 captured using measurement system 30 of FIG. 11A and shows measurement light 52M that includes a direct reflection region 120 (bottom) from light source 50. The narrow region 135 above the direct reflection region 120 is analyzed for measurement light 52M detected due to diffusion of light 52 caused by one or more types of surface defects 74. After full 360° rotation, all N intensity functions $<I_n(z)>$ are combined into a new 2D intensity function $<I_n(z,n)>$ that represents a combined digital image 72C of the entire circumference L of the surface of wound optical fiber 20W.

Figure 12B:
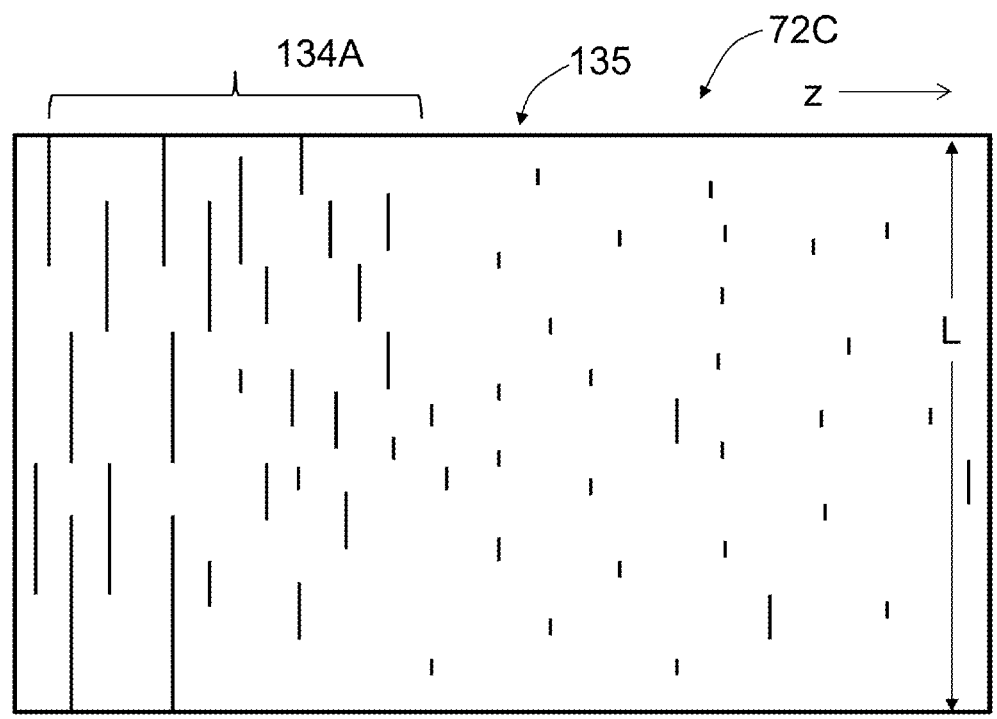
FIG. 12B is a schematic digital image of entire circumference of the surface of wound optical fiber shown as a negative image (i.e., black and white reversed) for ease of Illustration, wherein abrasion defects are revealed as the longer of the vertical lines.

FIG. 12B is a schematic view of a new digital image 73 of the entire circumference L of the surface of wound optical fiber 20W shown in the negative image (i.e., black and white reversed) for ease of Illustration. The dark lines thus depict detected measurement light 52M. The digital image 73 shows an abrasion defect 134A in coating outer surface 28 that manifests as elongated vertical lines in the digital image.

The combined digital image 72C of the entire circumference L of wound optical fiber 20W is processed using, in an example, standard skeleton binary filtration to calculate the total length of abrasion strikes 132. The result is compared to a threshold value, for a pass/fail judgment of abrasion defects 134A in spool 10.

Fifth Embodiment

Figure 13A:
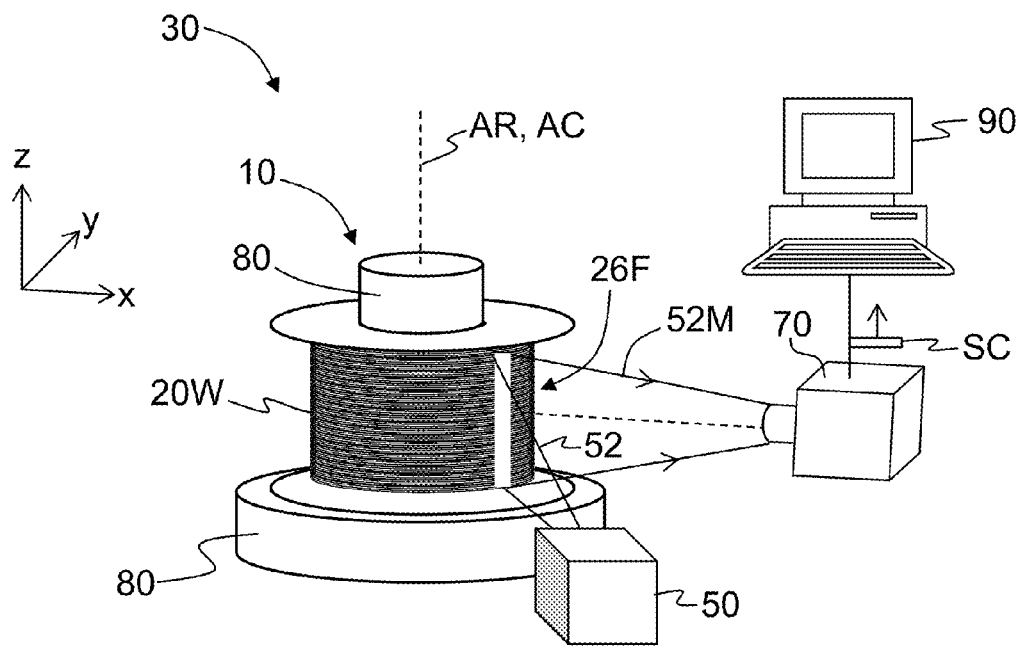
FIG. 13A is similar to FIGS. 3A, 7A, 9A and 11A and shows an example configuration of the measurement system for performing a measurement of defects in the wound optical fiber according to a fifth embodiment.
Figure 13B:
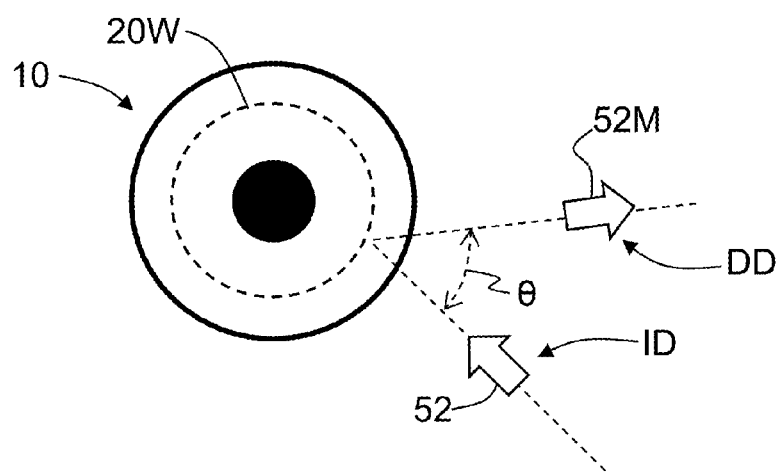
FIG. 13B is a schematic top-down view of the measurement system of FIG. 13A, showing the illumination and detection directions and the measurement angle.

FIG. 13A shows an example configuration of measurement system 30 similar to FIG. 11A but with light source 50 separated from digital camera 70 by a measurement angle θ that is less than 90° and in an example is between about 20° and 60°. To perform a measurement, spool 10 is rotated 360° while digital camera 70 captures a sequence of digital images (e.g., video images), e.g., tens to hundreds of frames. The digital images 72 can be real-time processed or post-processed and analyzed for defects 74. FIG. 13B is a top-down view of a portion of system 30 of FIG. 13A and shows an example measurement angle θ. FIG. 13A illustrates an example embodiment wherein support member 80 includes an axle.

Figure 14A:
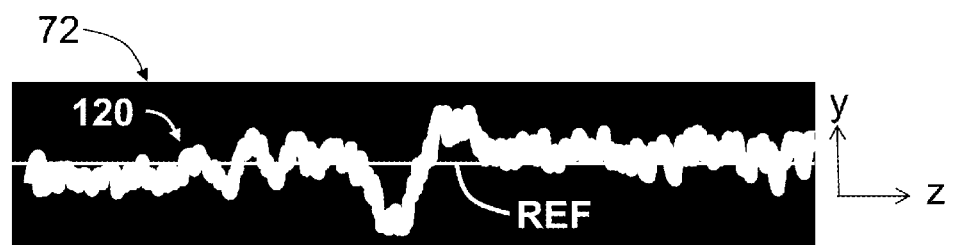
FIG. 14A shows a portion of a captured digital image that shows a variation in the measurement light reflected from the surface of the wound optical fiber.

FIG. 14A shows a portion of one of the captured digital images 72 (e.g., one of the n video frames). The white line 120 thus depicts a saturated reflection of measurement light 52M. In the case of an ideal cylindrical surface of spool 10 of wound optical fiber 20W in the region of reflection, measurement light 52M forms a perfectly straight line, shown as reference line REF.

Figure 14B:
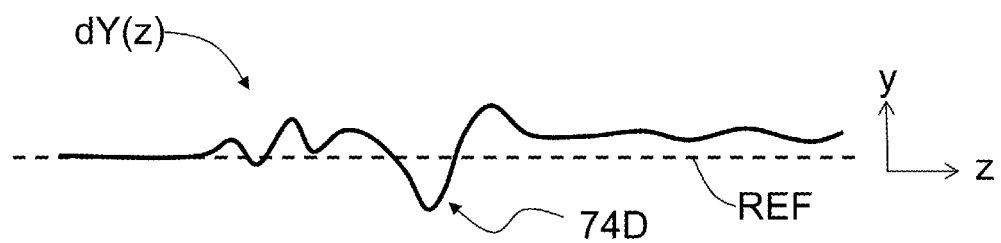
FIG. 14B shows an average variation dY(z) of the digital image of FIG. 14A relative to a horizontal reference line that shows a location of a dent defect in the surface of the wound optical fiber.

The average position of the line displacement dY(z) relative to a perfectly horizontal reference line REF along the z-axis is shown in FIG. 14B. This line displacement dY(z) represents a low frequency change in the slope of the fiber surface as compared to an ideal cylindrical shape. So function dY(z) represents SlopeY(z). The big perturbation represents a non-zero slope of a surface depression defect 74D. Such defects 74D can be caused, for example, by the flange of one spool 10 hitting the wound optical fiber 20W of another spool during handling or shipment.

Figure 14C:
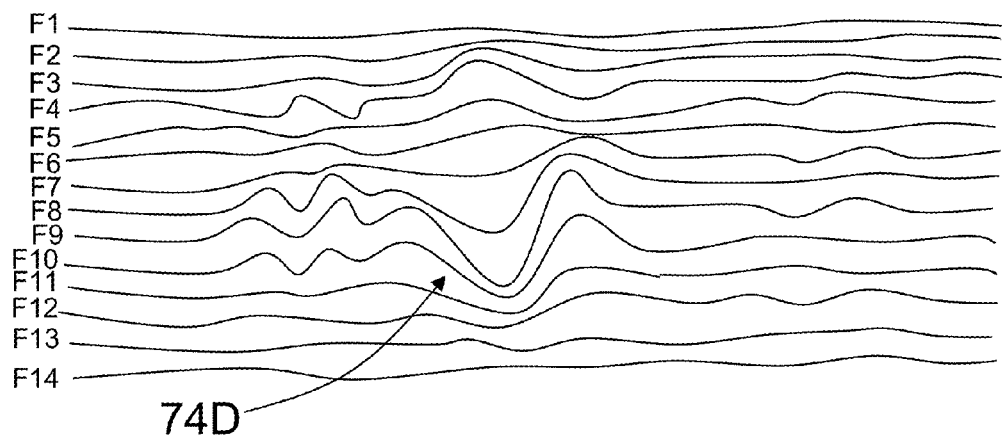
FIG. 14C schematically illustrates a combined result for dY(z) for fourteen digital image frames taken during rotation of the spool.

FIG. 14C schematically illustrates a combined result of dY(z) calculations from fourteen digital images 72 ("frames" F1 through F14) taken during a rotation of spool 10. A significant variation of slope between frames F2 through F12 can be seen, where the slope changes from negative to positive. This represents a region of surface depression or dent defect 74D. In an example, the processed functions dY(z) can be used to generate a 3D scanned surface representation of wound optical fiber 20W.

Figure 14D:
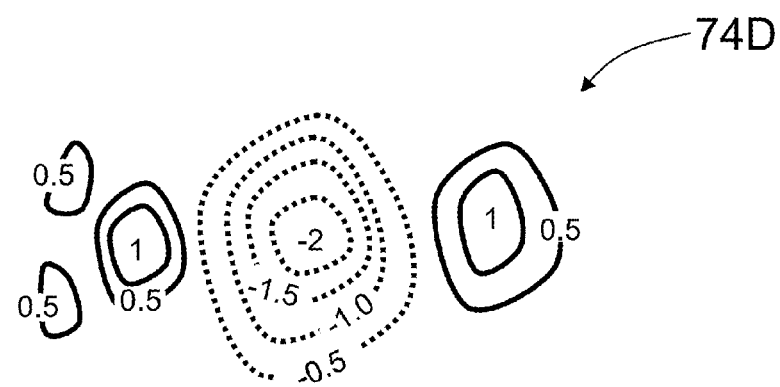
FIG. 14D shows a 3D scanned surface (contour plot) of elevation and depression defects as calculated by integrating the data from FIG. 14C along the Y-axis.

FIG. 14D shows a 3D scanned surface (contour plot) of elevation and depression regions (i.e., defects 74D) calculated by integrating the data from FIG. 14C along the Y-axis.

Figure 14E:
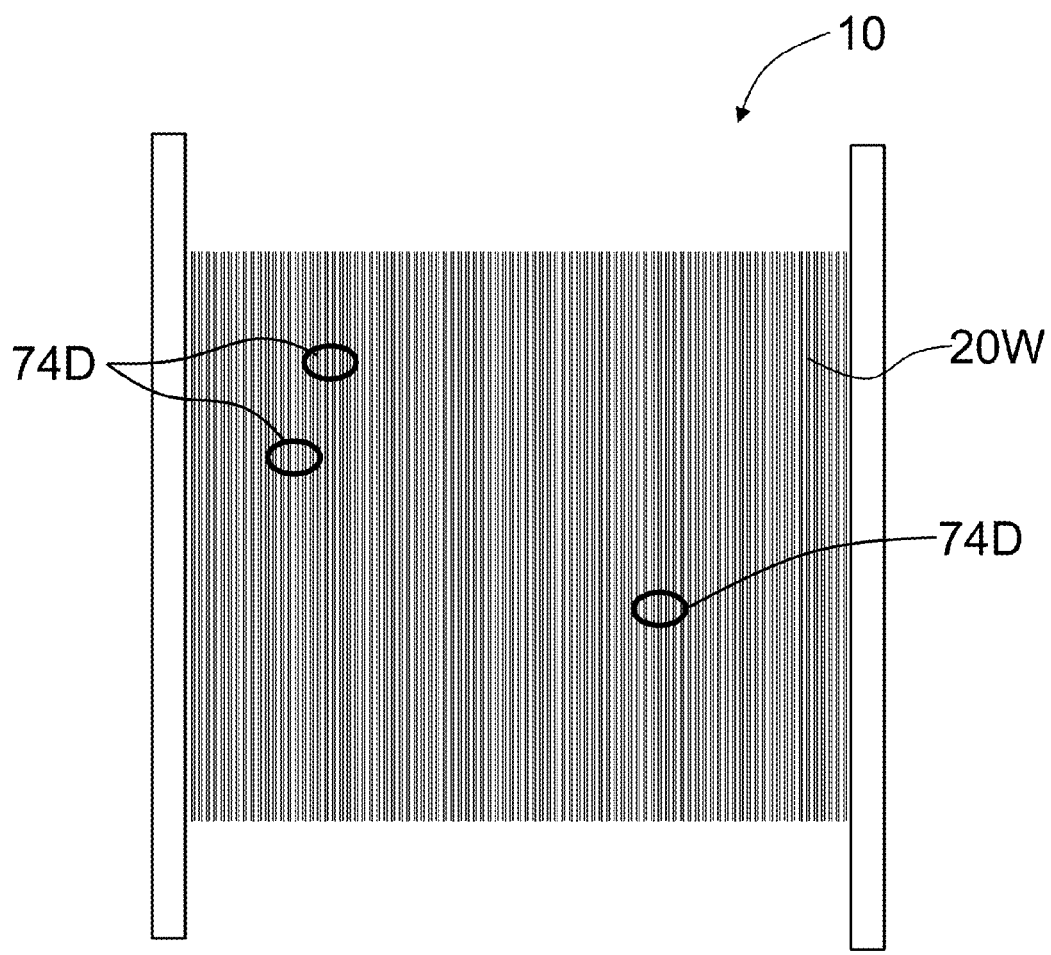
FIG. 14E shows an example spool with identified dent defects.

FIG. 14E shows spool 10 with dent defects 74D identified after processing digital images 72 and keeping track of the orientation of the spool during rotation so that the digital images can be matched to positions on wound optical fiber 20W. Calculated changes in the surface depression and elevation are then analyzed to characterize dent defects 74D, e.g., the size and depth of each dent. In an example, the 3D representation can be in the form of an intensity contour plot such as is shown in FIG. 14D.

Sixth Embodiment

Figure 15:
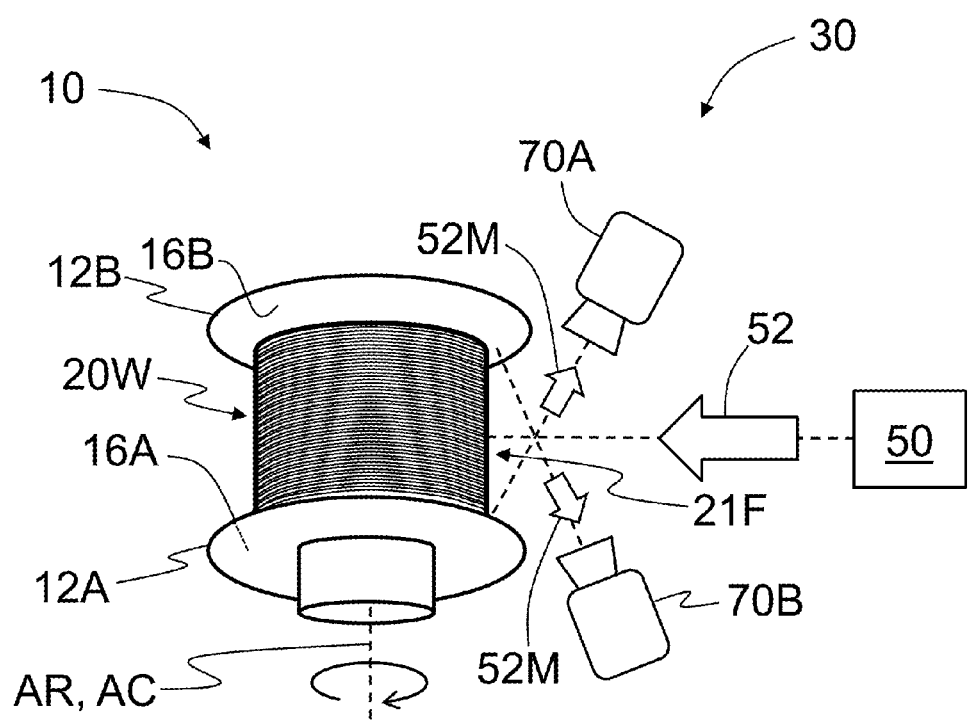
FIG. 15 is an elevated view of an example configuration of the measurement system for performing a measurement of defects in the wound optical fiber according to a sixth embodiment that employs two digital cameras.

FIG. 15 shows an example configuration of a portion of measurement system 30 that includes two digital cameras 70A and 70B. The light source 50 illuminates front side 21F of wound optical fiber 20W substantially straight on (i.e., at substantially normal incidence), while digital cameras 70A and 70B are directed to inner surfaces 16A and 16B of flanges 12A and 12B, respectively.

The spool 10 is rotated 360° and digital images 72 (e.g., several hundred video frames) are captured by each of digital cameras 70A and 70B. By directing digital cameras 70A and 70B to image the respective inside surfaces 16A and 16B of flanges 12A and 12B, measurement light 52M can be seen against the inside surfaces.

Figure 16:
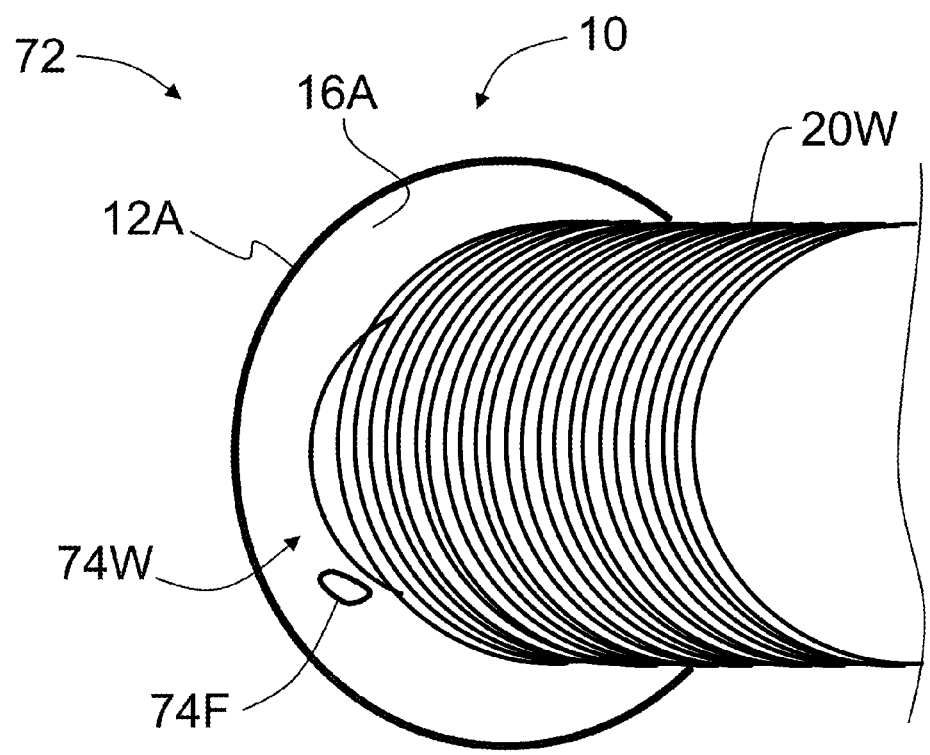
FIG. 16 is an example digital image of a spool as taken by one of the digital cameras of the measurement system of FIG. 15.

FIG. 16 is an image 72 of spool 10 and wound optical fiber 20W as taken by digital camera 70A. The image 72 of FIG. 16 shows a winding-error defect 74W in the form of a standalone single loop of optical fiber 20 up against inside surface 16A of flange 12A. A foreign object defect 74F (e.g., a piece of tape) visible on inside surface 16A of flange 12A is also visible.

Figure 17:
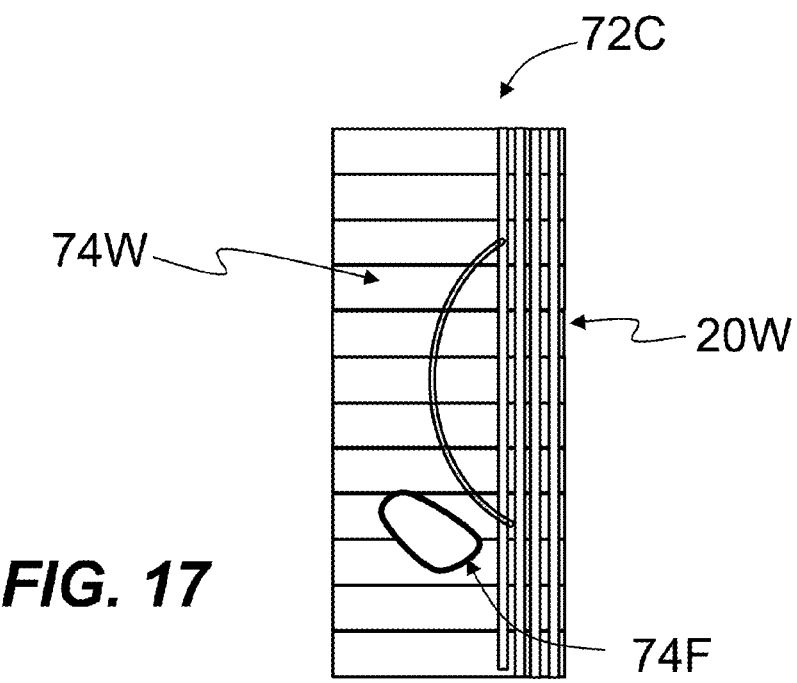
FIG. 17 shows a combined set of digital images acquired by one of the digital cameras during a 360° spool rotation using the measurement system of FIG. 15.

FIG. 17 shows an entire set of digital images 72 acquired during 360° spool rotation merged into a combined digital image 72C of the entire circumference of flange 12A. Both defects 74W and 74F are present on combined digital image 72C. Standard image processing, filtration, edge detection, skeleton and line detection algorithms are used to detect defects 74W and 74F against flange 12A, calculate metrics for the defects and then compare the results to a threshold, e.g., for a pass/fail/rework judgment for spool 10.

While measurement systems 30 described above have been described in connection with separate embodiments, it is noted that the single measurement system can be configured in a manner capable of performing the measurements of all the different embodiments described herein.

Furthermore, it will be apparent to those skilled in the art that various modifications to the preferred embodiments of the disclosure as described herein can be made without departing from the spirit or scope of the disclosure as defined in the appended claims. Thus, the disclosure covers the modifications and variations, provided they come within the scope of the appended claims and the equivalents thereto.

What is claimed is:

1. A method of inspecting a wound optical fiber on a spool having a front side and a back side, comprising:
    illuminating the wound optical fiber at the front side with illumination light from at least a first illumination direction, causing a portion of the illumination light to couple into the wound optical fiber and travel to the back side;
    capturing from at least one detection direction at least one digital image that includes measurement light formed by illumination light that is redirected out of the wound optical fiber at the back side; and
    processing the at least one digital image to detect and characterize at least one defect of the wound optical fiber.

2. The method according to claim 1, wherein the wound optical fiber includes a coating and wherein the illumination light that couples into the wound optical fiber couples into the coating.

3. The method according to claim 1, wherein the measurement light includes scattered light that appears as bright dots in the at least one digital image.

4. The method according to claim 1, further comprising rotating the spool about a central spool axis and capturing multiple digital images of the back side of the rotated wound optical fiber during the rotation.

5. The method according to claim 1, wherein the at least one defect is selected from the group of defects comprising: bubbles, abrasions, punctures, scratches, surface contamination, winding errors, periodic dimensional errors, aperiodic dimensional errors and dents.

6. The method according to claim 1, wherein the at least one digital image comprises multiple video frames, and further comprising rotating the spool while capturing the multiple video frames.

7. The method according to claim 1, wherein processing the at least one digital image includes performing at least one of: an average, a correlation, an autocorrelation, a convolution, a de-convolution, a Fourier transform and a filter.

8. The method according to claim 1, wherein capturing the at least one digital image comprises capturing first and second digital images along first and second detection directions.

9. The method according to claim 1, wherein the at least a first illumination direction consists of a single illumination direction as defined by a single light source.

10. The method according to claim 1, wherein the at least one digital image includes at least one edge of the wound optical fiber.

11. The method according to claim 9, wherein the at least one detection direction is a single detection direction and wherein the at least one digital image is captured by a single digital camera.

12. The method according to claim 10, further comprising comparing the at least one edge of the wound optical fiber as captured by the digital image to a reference.

13. A method of inspecting a wound optical fiber, comprising:
    illuminating the wound optical fiber with illumination light that optically couples into and travels within the wound optical fiber and that is redirected out of the wound optical fiber by at least one defect to generate measurement light;
    rotating the wound optical fiber;
    capturing a plurality of digital images of the wound optical fiber based on the measurement light during the rotation; and
    processing the plurality of digital images to characterize at least one defect of the wound optical fiber.

14. The method according to claim 13, wherein processing includes performing at least one of: an average, a correlation, an autocorrelation, a convolution, a de-convolution, a Fourier transform and a filter.

15. The method according to claim 13, wherein the at least one defect is selected from the group of defects comprising: bubbles, abrasions, punctures, scratches, surface contamination, winding errors, periodic dimensional errors, aperiodic dimensional errors and dents.

16. The method according to claim 13, wherein the plurality of digital images is captured by a plurality of digital cameras.

17. A system for inspecting for at least one defect in a wound optical fiber on a spool, comprising:
    a first light source arranged to illuminate the wound optical fiber with illumination light from a first illumination direction to cause a portion of the illumination light to optically couple into and travel within the optical fiber and to be redirected out of the wound optical fiber by the at least one defect as measurement light;
    a digital camera arranged to capture from a detection direction at least one digital image of the measurement light from the wound optical fiber; and
    a computer adapted to process the at least one digital image to characterize at least one defect of the wound optical fiber.

18. The system according to claim 17, wherein the at least one defect is selected from the group of defects comprising: bubbles, abrasions, punctures, scratches, surface contamination, winding errors, periodic dimensional errors, aperiodic dimensional errors and dents.

19. The system according to claim 17, wherein the computer is adapted to perform at least one process selected from the group of processes comprising: average, a correlation, an autocorrelation, a convolution, a de-convolution, a Fourier transform and a filter.

20. The system according to claim 17, wherein the at least one digital image comprises a plurality of digital images that cover an entire circumference of the wound optical fiber.

* * * * *